United States Patent
Tao et al.

(10) Patent No.: US 8,351,672 B2
(45) Date of Patent: Jan. 8, 2013

(54) MACHINE IMAGING APPARATUS AND METHOD FOR DETECTING FOREIGN MATERIALS

(75) Inventors: Yang Tao, North Potomac, MD (US); Xin Chen, Gaithersburg, MD (US); Hansong Jing, Hyatsville, MD (US); Bin Zhu, College Park, MD (US); Fenghua Jin, Beltsville, MD (US)

(73) Assignee: Industry Vision Automation Corp., Gaithersburg, MD (US)

( * ) Notice: Subject to any disclaimer, the term of this patent is extended or adjusted under 35 U.S.C. 154(b) by 1250 days.

(21) Appl. No.: 11/861,791

(22) Filed: Sep. 26, 2007

(65) Prior Publication Data

US 2009/0080706 A1      Mar. 26, 2009

(51) Int. Cl.
*G06K 9/00* (2006.01)
(52) U.S. Cl. ......... 382/132; 382/141; 250/370; 250/484
(58) Field of Classification Search .................. 382/132, 382/141; 250/582; 582/370.11
See application file for complete search history.

(56) References Cited

U.S. PATENT DOCUMENTS

| | | | |
|---|---|---|---|
| 5,198,669 A * | 3/1993 | Namiki et al. ................. | 250/587 |
| 5,420,441 A * | 5/1995 | Newman et al. .............. | 250/581 |
| 5,428,657 A | 6/1995 | Papanicolopoulos et al. | |
| 5,633,510 A * | 5/1997 | Rogers .......................... | 250/587 |
| 5,821,541 A * | 10/1998 | Tumer ..................... | 250/370.09 |
| 5,907,406 A | 5/1999 | Papanicolopoulos et al. | |
| 5,974,111 A | 10/1999 | Krug et al. | |
| 6,180,949 B1 * | 1/2001 | Leblans ...................... | 250/484.4 |
| 6,370,223 B1 | 4/2002 | Gleason et al. | |
| 7,304,309 B2 * | 12/2007 | Suhami .................... | 250/370.11 |
| 2003/0016781 A1 * | 1/2003 | Huang ............................ | 378/41 |
| 2007/0012777 A1 * | 1/2007 | Tsikos et al. .................. | 235/454 |

FOREIGN PATENT DOCUMENTS

WO      WO 2007/049305 A1      5/2007

OTHER PUBLICATIONS

Batistoni, P. et al.; Analysis of dose rate experiment: comparison between FENDL, EFF/EAF and JENDL nuclear data libraries; Fusion Engineering and Design 69; pp. 649-654, 2003.
Blake, Glen M. et al.; Dual energy X-Ray absoptiometry and its clinical applications; Seminars in musculoskeletal radiology, vol. 6, No. 3, pp. 207-218, 2002.
Carlsson, Torgny E.; Measurement of three-dimensional shapes using light-in-flight recording by holography; Opt. Eng., vol. 32, No. 10, pp. 2587-2592, 1993.

(Continued)

*Primary Examiner* — Vu Le
*Assistant Examiner* — Aklilu Woldemariam
(74) *Attorney, Agent, or Firm* — Westerman, Hattori, Daniels & Adrian, LLP

(57) ABSTRACT

A combined X-ray and laser 3D imaging system for food safety inspection, which uses a 3D laser subsystem to get accurate depth information, which is further combined with an x-ray image to achieve accurate physical contamination detection in poultry and other meat products. A unique calibration model is used to calibrate the x-ray and laser 3D imaging systems at the same time. And a nested multi-thread software structure is implemented to prevent data conflict and ensure fully use of system resources during the physical contamination detection of the poultry and other meat products.

16 Claims, 16 Drawing Sheets

OTHER PUBLICATIONS

Carlsson, Torgny E. et al.; System for acquisition of three-dimensional shape and movement using digital Light-in-Flight holography; Opt. Eng.; vol. 40, No. 1, pp. 67-75, 2001.
Casasent, D. et al.; Detection and Segmentation of Items in X-Ray Imagery; Transactions of the ASAE; vol. 44(2), pp. 337-345, 2001.
Casasent, D. et al.; New training strategies for RBF neural networks for X-ray agricultural product inspection; Pattern Recognition 36; pp. 535-547, 2002.
Chen F. et al.; Overview of three-dimensional shape measurement using optical methods; Opt. Eng.39, pp. 10-22, 2000.
Dowsett, David J. et al.; Physics of Diagnostic Imaging; London: Chapman & Hall Medical, 1998.
Duda, Richard O. et al.;. Pattern Classification. New York, NY: Wiley, 2000.
Genant, Harry K. et al.; Noninvasive Assessment of Bone Mineral and Structure: State of the Art. Journal of Bone and Mineral Research 11(6): pp. 707-730, 1996.
Graves, M. et al.; Design and analysis of X-ray vision systems for high-speed detection of foreign body contamination in food; Proc. SPIE 2347: pp. 80-92, 1994.
Haff, Ron P. et al.; Image restoration of line-scanned X-ray images. Opt. Eng. 36(12): 3288-3296, 1997.
Jalkio, Jeffery A. et al.; Three dimensional inspection using multistripe structured light. *Opt. Eng*. 24(6): 966-974, 1985.
Johns, Paul C. et al.; Dual-energy mammography: initial experimental results. *Med. Phys*. 12(3): 297-304, 1985.
Laplante, Phillip A. et al.; Real-time imaging: theory, techniques, and applications. New York, N.Y.: IEEE press, 1996.
Morita, Kazuo et al.; Development of soft X-ray imaging for detecting internal defects in food and agricultural products. In Proceedings from the Sensors for Nondestructive Testing Int. Conf., 305:315. Orlando, FL, 1997.
Nobel, J. et al.; High Precision X-ray Stereo for Automated 3-D CAD-Based Inspection. IEEE Transactions on Robotics and Automation. 14(2): pp. 292-303, 1998.
Papanicolopoulos, C. et al.; A feasibility study relative to the development of an on-line X-ray system that accurately detects bone and cartilage fragments in poultry meat. Final report to Southeastern Poultry & Egg Association, SPEA research project #80, 1992.
Ratnam, Mani Maran et al.; Three-dimensional object classification using shadow moiré and neural network Opt. Eng. 40(9): pp. 2036-2040, 2001.
Sandborg, Michael et al.; Influence of X-ray energy spectrum, contrasting detail and detector on the signal-to-noise ratio (SNR) and detective quantum efficiency (DQE) in projection radiography. Phys. Med. Biol. 37(6): pp. 1245-1263, 1992.
Schatzki, Thomas F. et al.; Visual detection of particulates in X-ray images of processed meat products. Opt. Eng. 35(8): pp. 2286-2291, 1996.
Sjodahl, M. et al.; Measurement of shape by using projected random patterns and temporal digital speckle photography. Appl. Opt. 38(10): pp. 1990-1997, 1999.
Smith, D. P.; Defects of pre- and post-deboned broiler breast. Journal of Applied Poultry Research 10: pp. 33-40, 2001.
Sorgel, Wolfgang, et al.; Efficient and accurate structured light algorithm for direct measurement of cylindrical surface parameters, 1997.
Toyooka, S. et al.; Automatic profilometry of 3D diffuse objects by spatial phase detection; Appl. Opt. 25; pp. 1630-1633, 1986.
Tsai, Roger Y., et al.; A Versatile Camera Calibration Technique for High-Accuracy 3D Machine Vision Metrology Using Off-the-Shelf TV Cameras and Lenses. IEEE Journal of Robotics and Automation3(4); pp. 323-344, 1987.
USDA; United States classes, standard, and grades for poultry; Washington, D.C.; USDA, 2002.
Jin, F. et al.; Geometrical calibration of a combined 3D laser and X-ray imaging system. SPIE. vol. 638 (2006):11-21, 2006.
Chen, Z. et al.; Food safety inspection using "from presence to classification" object-detection model. Pattern Recognition. vol. 34(2001):2331-2338, 2001.
Tao, Y. et al.; Internal inspection of deboned poultry using x-ray imaging and adaptive thresholding. Trans. of ASAE. vol. 44(4):1005-1009, 2001.
Chen, Z. et al.; Multi-resolution local multi-scale contrast enhancement of X-ray images for poultry meat inspection. Applied Optics. vol. 40(8):1195-2000, 2001.
Chen, Z. et al.; Wavelet-based adaptive thresholding method for image segmentation. Optical Engineering. vol. 40(5):868-874, 2001.
Tao, Y. et al.; Thickness invariant X-ray imaging detection of bone fragments in de-boned poultry meat—model analysis. Transaction of ASAE. vol. 43(2):453-459, 2000.
Chen, X. et al.; Pattern Classification for Boneless Poultry Inspection Using Combined X-ray/laser 3D Imaging. SPIE vol. 5996: 265-272, 2005.
Chen, X. et al.; Real-time Image Analysis for Nondestructive Detection of Metal Sliver in Packed Food. SPIE vol. 5996: 120-129, 2005.
Jing, H. et al.; Geometrical calibration and integration of laser 3D and x-ray dual systems. ASAE International Annual Meeting, Las Vages, NV. Jul. 27-30, 2003. ASAE Paper No. 036191. The American Society of Agricultural Engineering, St. Joseph, MI.
Jing, H. et al.; Analysis of factors influencing the mapping accuracy of x-ray and laser range images in a bone fragment inspecting system. ASAE International Annual Meeting, Las Vages, NV. Jul. 27-30, 2003. ASAE Paper No. 033086. The American Society of Agricultural Engineering, St. Joseph, MI.
Chen. X. et al.; Real-time detection of physical hazards in de-bonded poultry using high-resolution X-ray imaging. ASAE International Annual Meeting, Las Vages, NV. Jul. 27-30, 2003. ASAE Paper No. 033084. The American Society of Agricultural Engineering, St. Joseph, MI.
Chen, X. et al.; High-resolution real-time X-ray and 3D imaging for physical contamination detection in de-boned poultry meat. Photonics East. SPIE. Providence, RI. Oct. 2003.
Chen X. et al.; Minimum-Error Thickness Compensation for X-ray Inspection of Deboned Poultry Meat. ASAE paper 01-3062. The American Society of Agricultural Engineering, St. Joseph, MI. 2001.
Xin, C. et al.; X-ray absorption sensitivity of boneless poultry meat and possible contamination materials. *ASAE paper No. 99-3178* presented at the ASAE 1999 International Annual Meeting. Jul. 18-21, Toronto, Canada. The American Society of Agricultural Engineering, St. Joseph, MI.
Tao, Y, J. Ibarra, J. Walker, and M. Johnson. 1998. High-speed inspection of cooked meat using mm-level spectral digital imaging techniques. In *Proceeding of USDA Food Safety Consortium Annual Meeting*. pp. 84-90. Oct. 4-6, 1998. Kansas City, MO.

\* cited by examiner

Fig. 4(a)
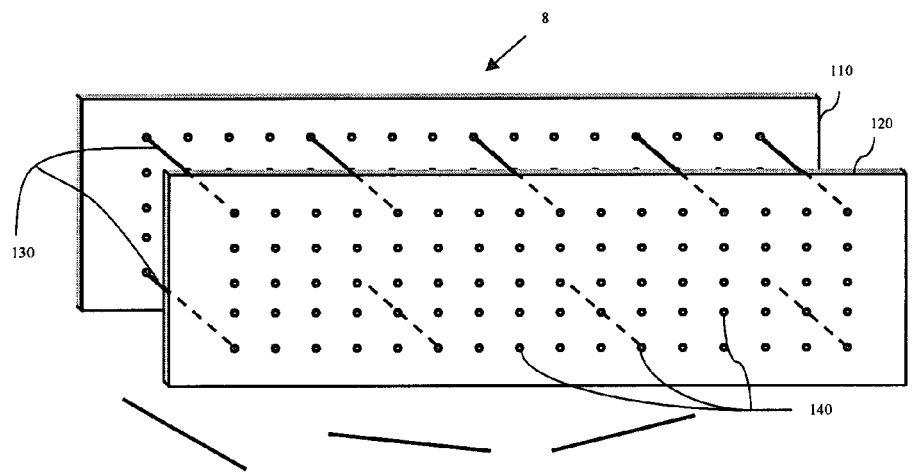
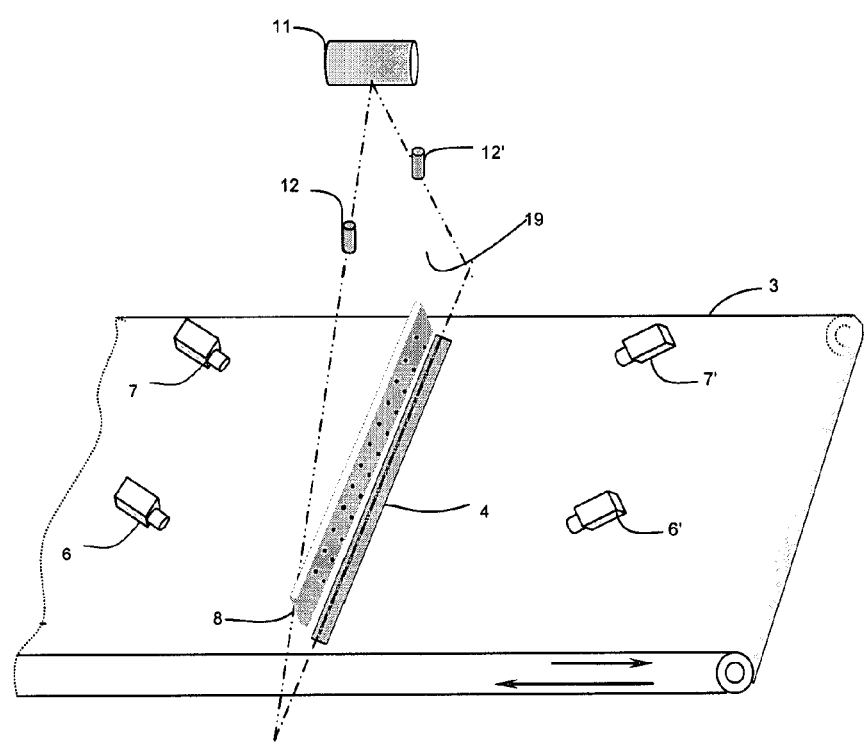
Fig. 4(b)

LW: Locator Worker        PW: Probe Worker

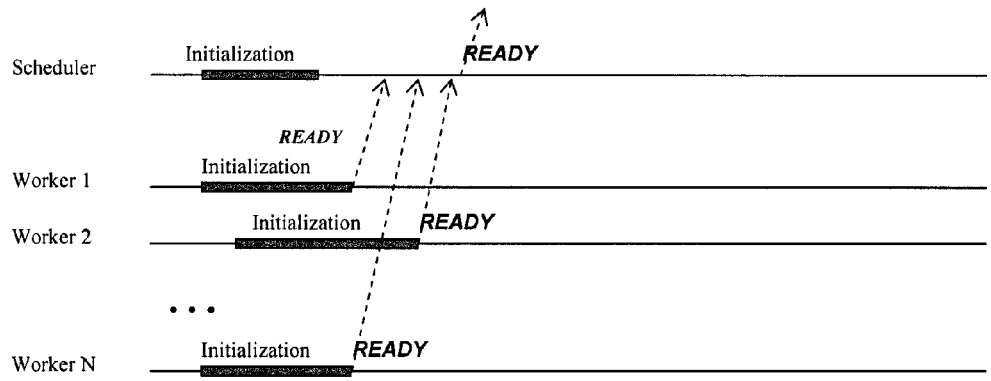
Fig. 18(a) Initialization phase
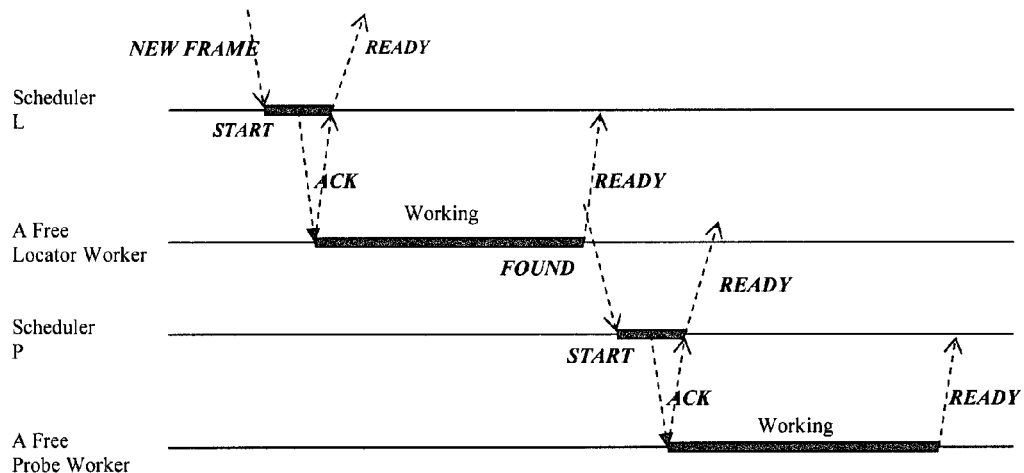
Fig. 18(b) Processing phase

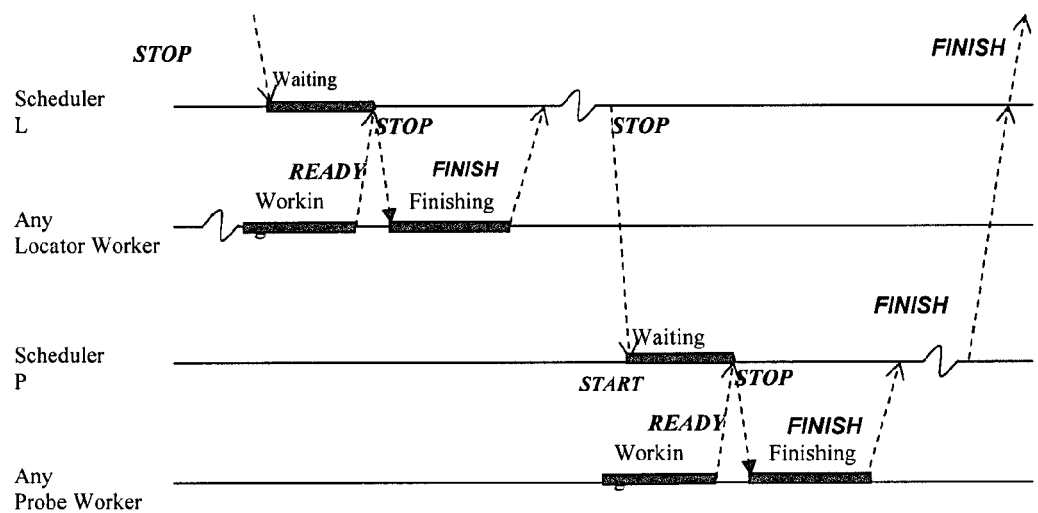
Fig. 18 (c) Termination phase

MACHINE IMAGING APPARATUS AND METHOD FOR DETECTING FOREIGN MATERIALS

BACKGROUND OF THE INVENTION

1. Field of the Invention

The present invention relates to a system and method for detecting bone fragments and foreign materials in poultry and other meats. More specifically, the present invention relates to using x-ray imaging and laser imaging techniques to detect bone fragments, cartilage, etc, and other foreign materials in meats, particularly poultry fillets.

2. Description of Related Art

Physical contamination is one of the major types of contamination compromising food safety. In boneless poultry meat, physical hazards include plastic, metal, glass, bone fragments, etc., which can lead to serious injury if ingested by the consumer. To ensure food quality and food safety, it is necessary for poultry processors to inspect each piece of boneless poultry and to make sure that bone fragments and any other unwanted hazardous materials such as metals and plastics do not remain in the product.

X-ray imaging techniques, as noninvasive inspection methods, have been used for years to detect physical contamination in food products. However, traditional x-ray inspection systems currently being used to detect bone fragments in poultry fillets have a high rate of failure (over 30%). As suggested by numerous publications and industrial reports, x-ray inspection systems cannot succeed in detecting bone fragments in poultry unless the challenge of uneven meat thickness is addressed. Generally, the intensity (or grayscale) of an object in an x-ray image reflects the x-ray absorption, which is dictated by the physical characteristics of the material and its thickness. As such, traditional x-ray imaging detection technologies have significant difficulties in detecting food contaminations because of variations in food thickness.

One thickness cancellation method adopted by the industry is to press the meat mechanically. A pump is used to press the meat into a pipe, compressing it into a rectangular block of uniform thickness before it is scanned by an x-ray imager. It was reported that the method worked particularly well for ground meat inspection. However, for products such as poultry fillets, where the preservation of the natural shape is desired this compression method is unattractive due to the inevitable meat damage. Furthermore, once the X-ray machine reports a contamination in the pipe, it is often difficult for human inspectors to determine the exact location of the defect in the chunk of rejected meat.

Other than a single energy based x-ray imaging, dual x-ray imaging technology has also been investigated by researches due to its capability in differentiating the different materials based on their respective responses to different x-ray energy level. However, limitations of this dual energy method come from the underlying physics. Compared to the human body, poultry fillets are much thinner and softer, thus in order to have high quality x-ray images, it is necessary to use lower energies than those for medical radiography. This requirement implies that the difference between the high and low energies is small, which leads to an insufficient contrast between the images taken at the two energies.

Imaging technologies other than x-ray imaging have also been adopted by researches for detecting foreign material in food products. Laser irradiation imaging has been used in which a laser beam is used to scan food products. The presence of undesired ingredients can be determined when variations in the intensity of the laser beam passing through the food products are found. However, such systems also have a higher failure rate than desired, since they are not capable of capturing a true profile of the surface of a meat product due to undetected surface bumps or other hidden occlusions on the surface.

SUMMARY OF THE INVENTION

In order to overcome the problems described above, preferred embodiments of the present invention provide a system and method that use an x-ray imaging and laser imaging system for food safety inspection.

Preferred embodiments of the present invention also provide a 3D laser system that is used to get the depth information, which is further combined with an X-ray image to achieve accurate physical contamination detection.

Preferred embodiments of the present invention also provide that a tight cabinet that is specially designed to be water tight and to avoid moisture condensation.

Preferred embodiments of the present invention also provide a unique calibration model and corresponding algorithms that are used to calibrate both the X-ray and laser 3D imaging system.

Preferred embodiments of the present invention also provide a multi-thread software structure that is implemented to prevent data conflict and ensure fully use of the system resources.

BRIEF DESCRIPTION OF THE DRAWINGS

FIGS. 4($a$) and 4($b$) illustrate a calibration model which is used to calibrate both the X-ray and laser 3D imaging systems and a configuration showing the set up of the calibration model during system calibration, respectively, according a second preferred embodiment of the present invention.

FIGS. 18(a)-18(c) illustrate timing diagrams of message control and synchronization realized in the initialization phase, the processing phase and the termination phase in the multi-thread system, respectively.

DETAILED DESCRIPTION OF PREFERRED EMBODIMENTS

Figure 1:
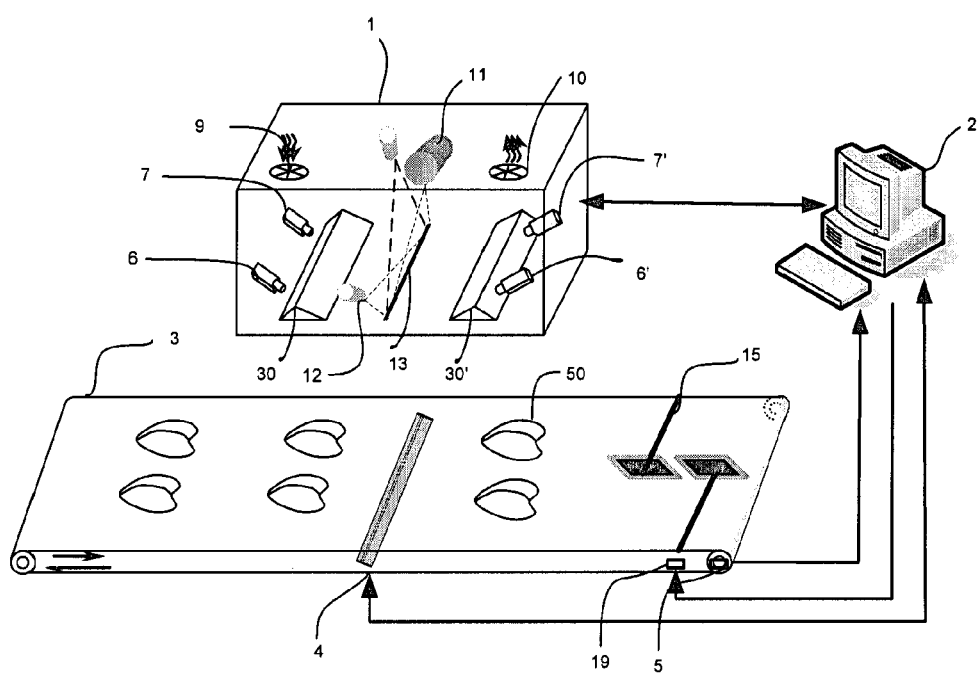
FIG. 1 illustrates a configuration of a food safety inspection apparatus, which includes both an x-ray imaging and a 3D laser imaging system according to a first preferred embodiment of the present invention.

Preferred embodiments of the present invention will be described with reference to the accompanying drawings. FIG. 1 illustrates a configuration of a food safety inspection apparatus, which includes both an x-ray imaging and a 3D laser imaging system according to a first preferred embodiment of the present invention. With initial reference to FIG. 1, the first preferred embodiment of the present invention is described in terms of an apparatus for detecting foreign materials inside poultry fillets. However, the present invention can also be applied to other types of agricultural products, such as beef or seafood and even non-agricultural commodities for detecting surface and internal characteristics thereof.

As shown in FIG. 1, an endless conveyor 3 holds, carriers and transfers objects 50 (i.e., chicken fillets) for inspection. When the conveyor 3 is moving, an encoder 5, attached at the rotation axis of the conveyor 3, monitors the movement of the conveyor 3 and provides signals to a computer 2 to control and synchronize cameras (6, 6', 7, 7') and an x-ray line-scan camera 4 with the movement of the conveyor 3. The computer 2 includes signal processing capability, such as a CPU (not shown), which processes the signals from the encoder 5 and sends synchronization signals to cameras (6, 6', 7, 7') and the x-ray line-scan camera 4. For the first preferred embodiment shown in FIG. 1, first and second pairs of camera (6, 6') and (7, 7') are used to provide a 3D profile of the scanned objects based on a structured lighting method. The number of camera pairs can be easily changed based on the width of the conveyor 3. And, for each pair of cameras (6, 6', 7, 7'), one camera is placed on each side of the x-ray tube 11, as shown in FIG. 1. The x-ray line-scan camera 4 under the conveyor 3 is used to capture the x-ray image of an object 50. The entire image data of the object 50 captured by cameras (6, 6', 7, 7') and x-ray line-scan camera 4 is transferred to the computer 2 for further image processing. If any bone, bone fragments or foreign material(s) is detected within or on the surface of the product 50 by the computer 2 during the image processing, it can be removed off the conveyor 3 by the rejection device 15 via the actuator 19 in real time.

As shown in FIG. 1, electronic devices located inside a water tight cabinet 1 consume electricity and generate heat when they are working. The temperature inside of cabinet 1 will increase with time while the temperature outside of cabinet 1 is low and almost constant. This temperature difference will cause moisture condensation on the cabinet's 1 inside surface. To prevent this problem, cool and dry air is pumped into the cabinet 1 through the opening 9. After the air circulates inside the cabinet 1, the air then leaves the cabinet 1 from the opening 10 carrying the heat out with it. As such, condensation inside of the cabinet 1 can be prevented.

In order for the system to work properly, it is important to carefully align each of the imaging devices such as the: x-ray tube 11, laser sources 12, 12', cameras (6, 6', 7, 7'), x-ray line-scan camera 4 and the plastic or glass window 13. As shown in FIG. 2, the laser beams 14, 14' generated respectively by the laser sources 12, 12' and the x-ray fan beam 19 generated by the x-ray tube 11 are adjusted to be coplanar with each other when the whole system is setup. The x-ray fan beam 19 needs to be further adjusted to pass through the center of the plastic or glass window 13, as shown in FIG. 1, so that it is able to hit the x-ray line-scan camera 4 under the conveyor 3. Cameras (6, 6', 7, 7') can see through the transparent plastic window 30, as shown in FIG. 1, and capture images of the object(s) 50 placed on the surface of the conveyor 3. A 3D profile of the observed object(s) 50 can be reconstructed based on the structured lighting method. Cameras (6, 6', 7, 7') are installed at both sides of the laser beams 14, 14' to decrease the occlusion problem. Therefore, image data from each camera of the pair of cameras 6, 6' (7, 7'), on each side of the laser beam 14 (14') will be processed together to get better a 3D profile of the object 50 on the conveyor 3.

Since cameras (6, 6', 7, 7') at each side of the laser beams 14, 14' need to see through the transparent windows 30, 30' the orientation of the CCD cameras (6, 6', 7, 7') with respect to the windows 30, 30' is important. In order to reduce light reflection from the surface of windows 30, 30', the cameras (6, 6', 7, 7') are placed perpendicular or substantially perpendicular to the windows 30, 30'. The position and orientation of the window(s) 30, 30' are carefully calculated based on the geometrical relationship between the x-ray tube 11, the laser sources 12, 12', the cameras (6, 6', 7, 7'), x-ray line-scan camera 4 and the height of the conveyor 3. Although, three separate windows 13, 30 and 30' are shown in FIG. 1, it is understood that these three separate windows could be replaced by a single window or a combination of windows.

Figure 2A:
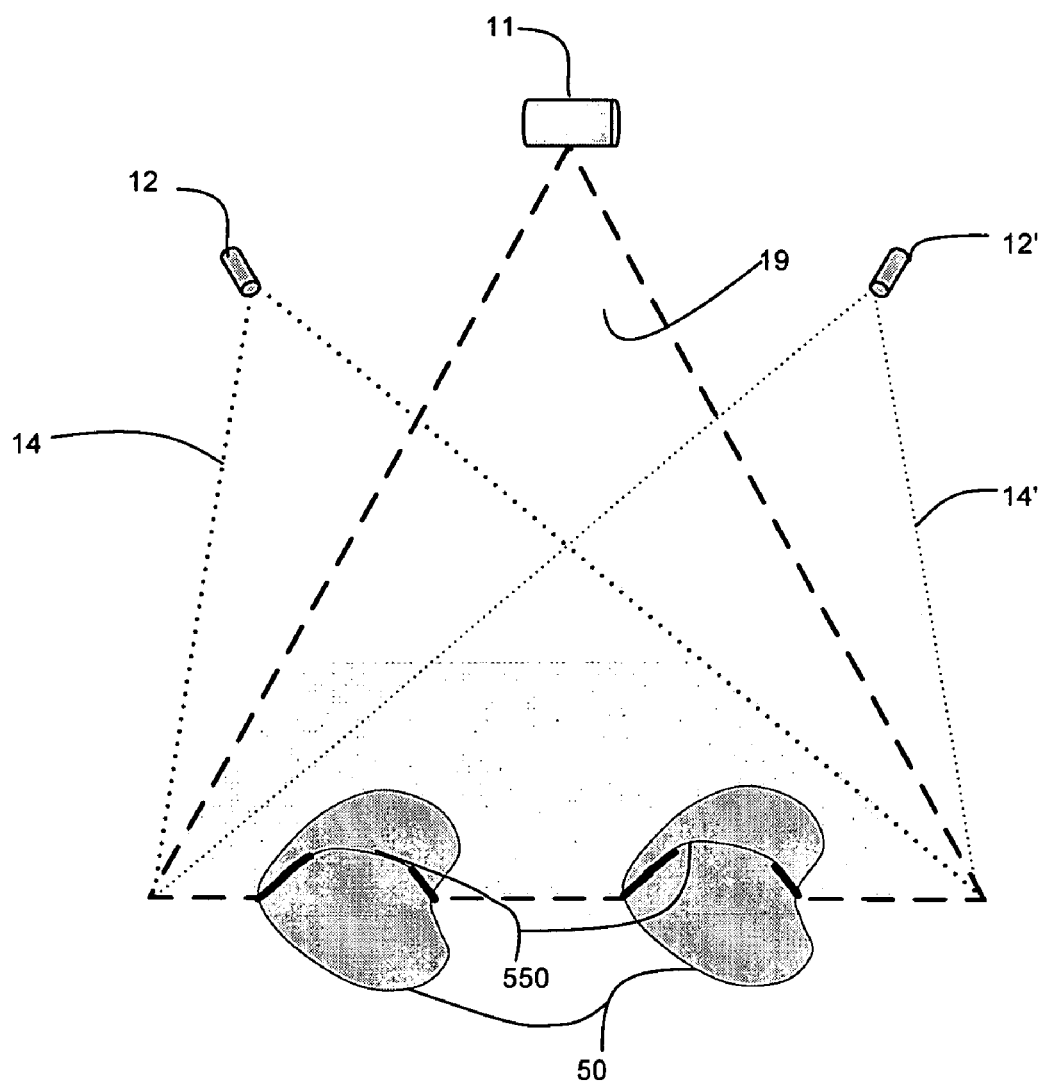
FIGS. 2($a$) and 2($b$) illustrate a configuration of the alignment between the X-ray and laser 3D imaging system to fully capture the laser projection line of two beams superimposed to compensate for side occlusions.

As shown in FIG. 2a, the x-ray tube 11 and the two lasers 12, 12' can be specially placed on each side of the x-ray tube 11 and can be tilted at an angle (in a predetermined range between 5 to 85 degrees off the vertical axis depending on the average height of the object(s) 50 on the conveyor 3) in order to reduce the occlusions of the side edges of the object 50 during 3D surface reconstruction. The two side lasers 12, 12' are titled in an angle in order to allow the cameras (6, 6', 7, 7') to see the sides of the objects 50 illuminated by lasers 12, 12'. As discussed above, the two laser beams 14, 14' and the x-ray beam 19 are coplanar or substantial co-planer. In addition, the two lasers 12, 12' are placed at each side of the x-ray tube 11 at an angle and are both oriented toward the surface of the conveyor 3. Therefore, when the object(s) 50 intersect with the laser beams 14, 14', the laser line 550 projected on the object's 50 surface will be less occluded (the occlusion can be caused by its bumpy surface and it usually happens at the position highlighted sections of 550 in the FIGS. 2a and 2b). The two laser beams 14, 14' overlap and compensate for each other in the way that both left and right sides of the objects(s) 50 on the conveyor 3 can be illuminated and seen by the cameras (6, 6', 7, 7').

Figure 2B:
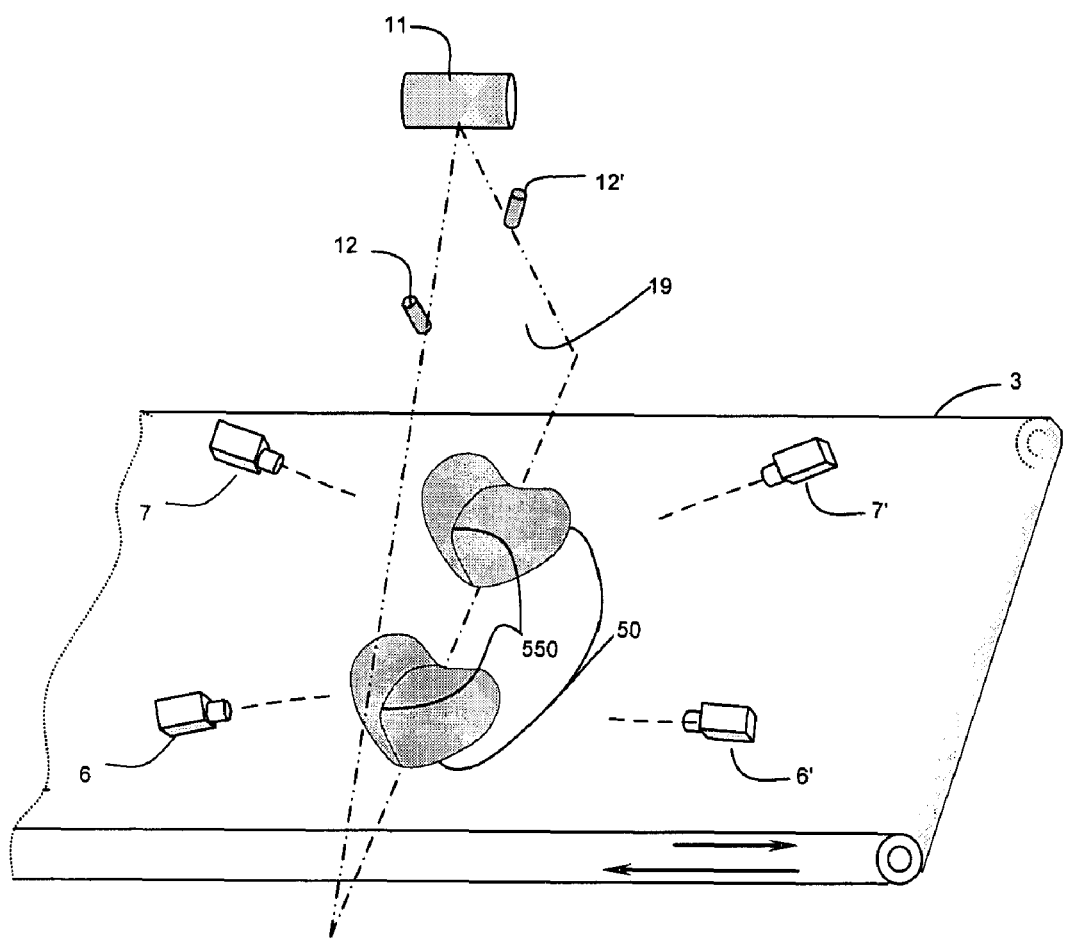

As shown in FIG. 2b, the first and second pair of cameras (6, 6', 7, 7') at both sides of the x-ray beam 19 and laser beams 14, 14' are also specially placed to fully capture the laser projection line (two beams superimposed and compensated for side occlusions). All the cameras (6, 6', 7, 7') near the conveyor's 3 edge are oriented angularly (in a predetermined angle range between 2 and 80 degrees from the conveyor moving direction) toward the conveyor center which makes them able to see the side edge part (highlighted sections of 550) of the laser projection line 550 on the object(s) 50.

As noted earlier, the cameras (6, 6', 7, 7') on each side of the x-ray beam 19 and laser beams 14, 14' are set in such a manner that if a bumpy surface of a meat object (hilly) blocks the view of one camera 6, 7 of the laser beam 14, then the other camera 6', 7' on the opposite side can see the laser beam 14'. Thus, at least one camera (6, 6', 7, 7') will see a laser beam 14, 14' on the object(s) 50 regardless of occlusion due to the bumpy meat surface.

Figures 3A, 3B, 3C, 3D, 3E:
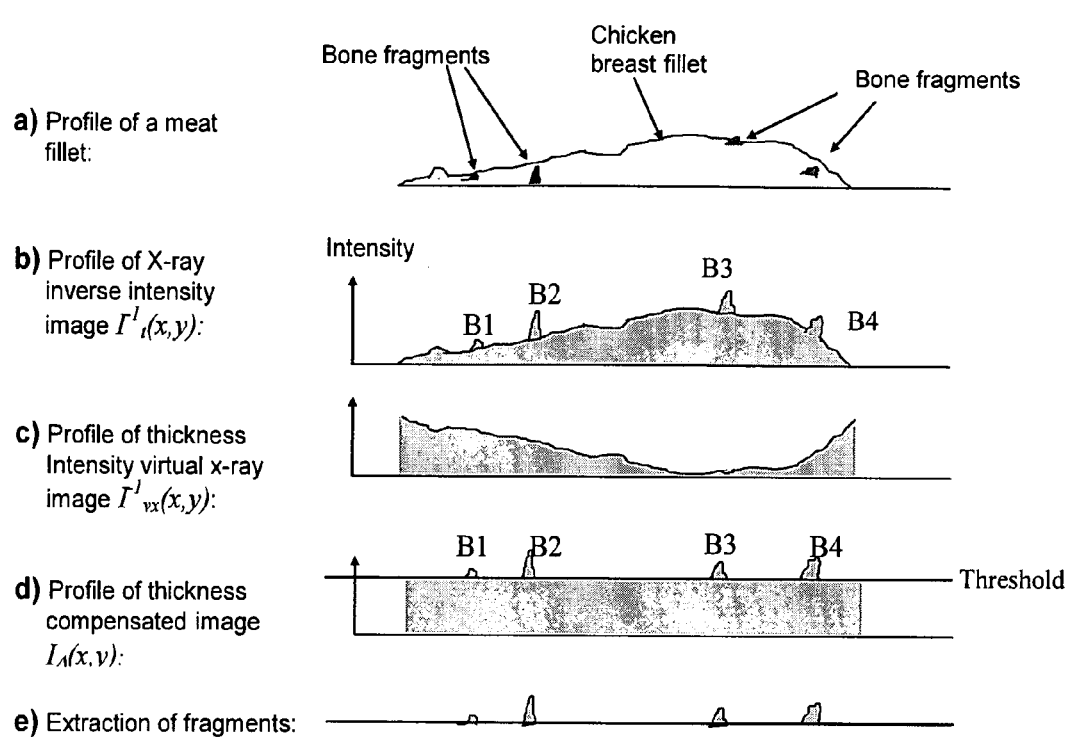
FIG. 3($a$) is a profile plot of a sample having bone fragments and FIGS. 3($b$)-3($e$) show general processing steps for detecting the bone fragments according to an embodiment of the present invention.

FIGS. 3(a)-3(e) illustrate the conceptual procedure of the sensor fusion scheme. FIG. 3(a) shows a chicken fillet containing bone fragments. Its x-ray image (inverted for visualization) is in FIG. 3(b). The surface topography is obtained using laser range imaging, and then the 3D thickness image is mapped to a virtual x-ray image as shown in FIG. 3(c). By combining the mapped image with x-ray image, the thickness-compensated x-ray image is obtained as shown in FIG. 3(d). Finally, the embedded bone fragments are segmented as shown in FIG. 3(e).

Because both x-ray and laser depth images are function of thickness, a mapping relationship exists between them. The transformation of a depth image $T(x, y)$ to a virtual x-ray image $I_{vx}(x,y)$ can be obtained by mapping:

$$I_{vx}(x,y) = f(T(x,y))$$

The mapping function can be determined with chicken meat containing no bone inclusions. The mapping can be constructed through a lookup table or fitted to an analytical function such as by a quadratic fitting function as:

$$I_{vx}(x,y) = f(T(x,y)) = aT^2(x,y) + bT(x,y) + c$$

Where a, b, c are fitting coefficients determined at run-time by experiments. Notice, for different x-ray energy settings, the values may vary. Run-time calibrations may be needed, as is typical practice for online systems. In ideal case, the mapping function results in:

$$I_{vx}(x,y) = I_t(x,y)$$

i.e., the transformed virtual x-ray image $I_{vx}(x,y)$ would be visualized just like the x-ray image of meat $I_t(x, y)$, no bone fragment inclusions show in the virtual x-ray image. Thus, we eliminate the thickness effect by subtraction:

$$I_\Delta(x,y) = I_{vx}(x,y) - I'_t(x,y) = I_t(x,y)(1 - e^{-\delta T_2})$$

Figure 6:
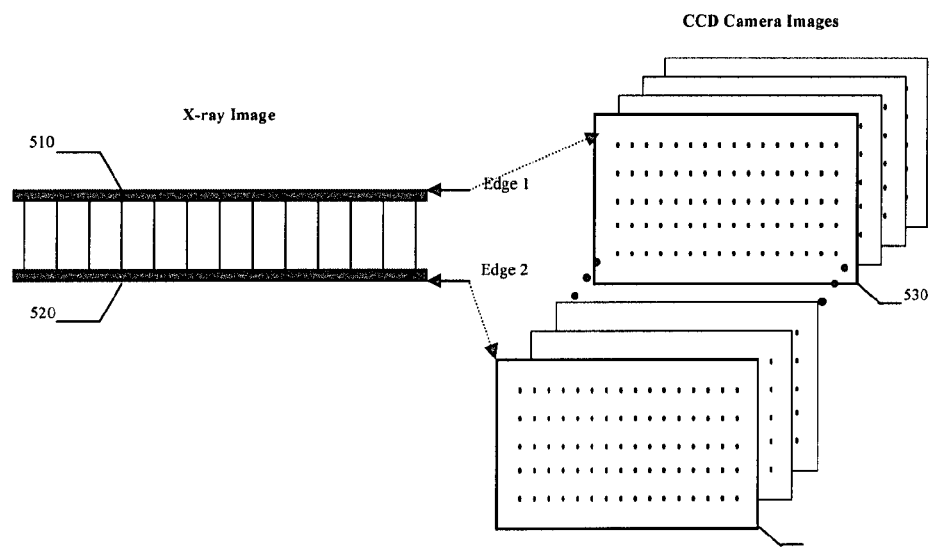
FIG. 6 illustrates a configuration of how the CCD camera calibration images are automatically selected by using the information from the X-ray image of the calibration model.

Or similarly, as illustrated in FIG. 6, $$I_\Delta(x,y) = C - [I_{vx}(x,y) + I'^{-1}_t(x,y)]$$

Note that $I'_t(x, y)$ denotes x-ray image of meat with bone inclusions. C is a maximum image constant to prevent image underflow, and $I'^{-1}_t(x, y)$ is the inverse image of $I'_t(x, y)$.

As a result, the difference image $I_\Delta(x,y)$ is independent of meat thickness. In principle, if chicken meat contains no foreign inclusion, $I_\Delta(x,y)$ is zero (0). Nonzero values in $I_\Delta(x, y)$ indicate inclusions. In practice, to eliminate any residual or image noises resulting from imperfect thickness compensation, the object segmentation can be rendered by thresholding with a small constant $\epsilon$. If a pixel in $I_\Delta(x,y)$ is >0, then it contributes to inclusion, otherwise, it is meat.

FIG. 4(a) is a diagram showing a unique calibrate model to calibrate both types of cameras, that is, the x-ray line-scan camera 4 and the CCD cameras (6,6',7, 7') according to a second preferred embodiment of the present invention. The calibration model 8 is composed of two flat metal plates 110 and 120 and steel pins 130 inserted between at known geometrical positions. On the surface of each flat metal plate 110, 120, there are small holes 140 made by a CNC (Computer Numerical Controlled) machine so that the physical coordinates of each hole 140 is precisely controlled. The holes 140 on the surface of plates 110, 120 are used to calibrate CCD cameras (6, 6', 7, 7') while the steel pins 130 inserted between the two flat metal plates 110, 120 are used to calibrate the X-ray line-scan camera 4.

To calibrate the whole system, as shown in FIG. 4(b), the calibration model 8 needs to be placed on the conveyor 3 and parallel to the plane of the x-ray beam 19 or the laser beams 14, 14'. When the calibration model 8 moves slowly with the conveyer 3 from left to right, its first metal plate surface (i.e., 120) will be coplanar with plane 19 followed by the second metal plate surface (i.e., 110). The image captured by the CCD camera(s) (6, 6', 7, 7') when the metal plate surface 110, 120 is coplanar with the plane 19 will be used to calibrate that camera. When the calibration model 8 moves through the plane 19, the x-ray image captured by the x-ray line-scan camera 4 will be used to calibrate the x-ray line-scan camera 4.

Figure 5A:
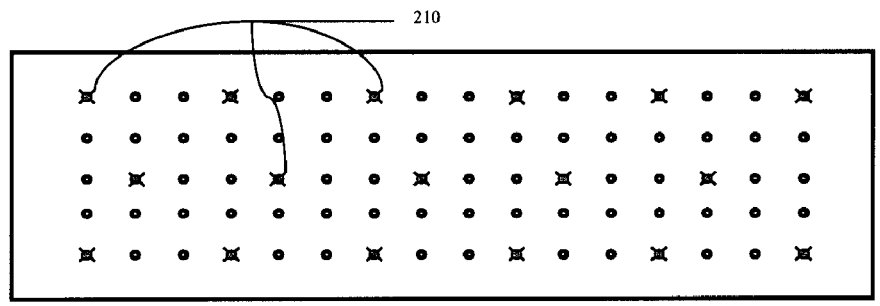
FIGS. 5($a$)-5($c$) illustrates a side view of the calibration model, an X-ray image of the calibration model and the geometrical principle to achieve image registration for any neighboring cameras, respectively.

FIG. 5(a) illustrates a side view of the calibration model 8 which shows the locations where pins 210 are inserted to calibrate the x-ray line-scan camera 4. These locations can vary. However, to achieve high calibration precision, these pins are located in wider distribution and cover the field of view (FOV) of the CCD cameras (6, 6', 7, 7'). Also the total number of these pins is also not fixed. Basically, as long as each pin 210 in the x-ray image doesn't overlap each other, increasing the number of pins 210 can improve the calibration precision.

Figure 5B:
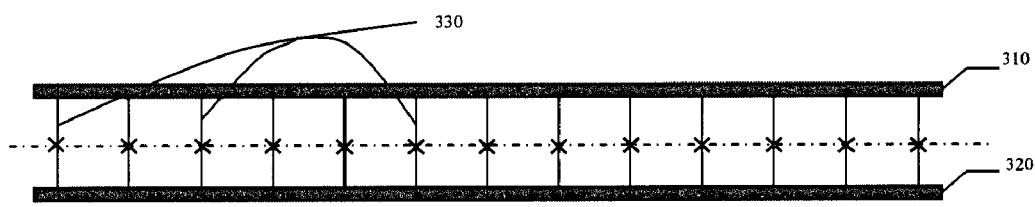

FIG. 5(b) illustrates an x-ray image captured by x-ray line-scan camera 4 when the calibration model 8 moves with the conveyor belt 3. X-ray images 310 and 320 are of the two metal plates 110 and 120, respectively. And X-ray image 330 is of the metal pins 130 inserted between. The coordinates of a set of feature points (cross sign in FIG. 5(b)) can be obtained after image processing. The relationship between these image coordinates and the corresponding physical coordinates (metal pins are placed at known position) are used to calibrate the x-ray line-scan camera 4 based on the 2D pin-hole camera model.

Figure 5C:
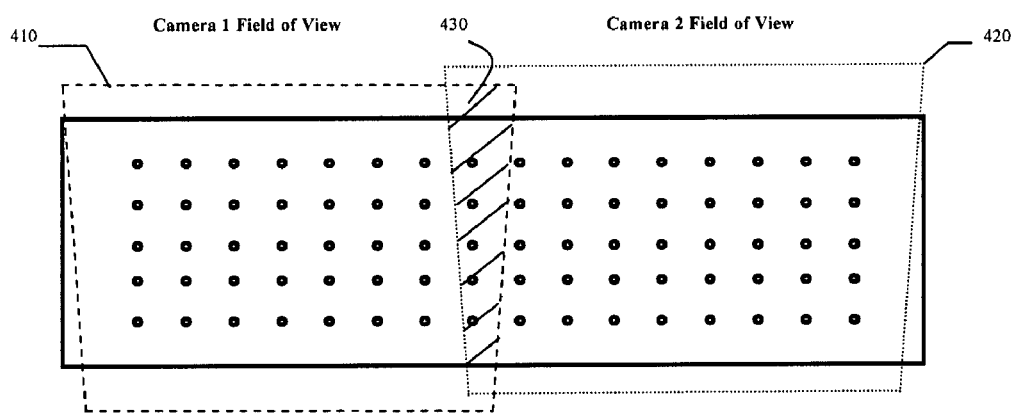

FIG. 5(c) shows the side view of the calibration model 8. The hole patterns 140 are used to calibrate the corresponding CCD cameras (6, 6', 7, 7') based on the 3D pin-hole camera model. Due to the geometrical limitation, the FOV of one camera at the working distance is limited. If a wider cover area is desired more cameras have to be added with proper camera image registration. Here in FIG. 5(c), it is only shown how to register images of two neighboring cameras 6, 7; however, this method can be easily extended to register any number of cameras. The two quadrangles 410 and 420 represent field of view (FOV) of two cameras 6, 7 and the shading area 430 is the FOV overlap. So any point in the shading area 430 can be seen by both cameras 6, 7 which suggests to combine information from both cameras 6, 7 to achieve better registration precision at the shading area 430.

System calibration is usually time-consuming and has high technical requirement. An automatic calibration method can both reduce human interaction and save time. One critical step to achieve automatic system calibration is how to select the calibration image automatically. This is explained in FIG. 6. As discussed previously, when the calibration model 8 moves with the conveyor belt 3, the signal from the encoder 5 will trigger both the x-ray line-scan camera 4 and CCD cameras (6, 6', 7, 7') to capture images at the same time. An example of the x-ray image captured by the x-ray line-scan camera 4 and the corresponding sequence of images grabbed by CCD cameras (6, 6', 7, 7') are shown in FIG. 6. The x-ray image can be used for the x-ray line-scan camera 4 calibration. However, not all of the images captured by a CCD camera 6 can be used to calibrate that CCD camera. Actually only the image grabbed when the metal plate 110, 120 of the calibration model 8 is coplanar with the plane 19 or laser beam 14 is useful. Therefore, the x-ray image 540 of the calibration model 8 is selected to correct images for CCD camera 6 calibration. Two edges (510 and 520) of the calibration model 8 are first detected by using image processing algorithm in the computer 2. The locations of the edges 510 and 520 are used to select the images to calibrate the corresponding CCD cameras 6 since both the x-ray line-scan camera 4 and CCD cameras (6, 6', 7, 7') are synchronized. Each selected image is used to calibrate the corresponding CCD camera (6, 6', 7, 7').

Figure 7:
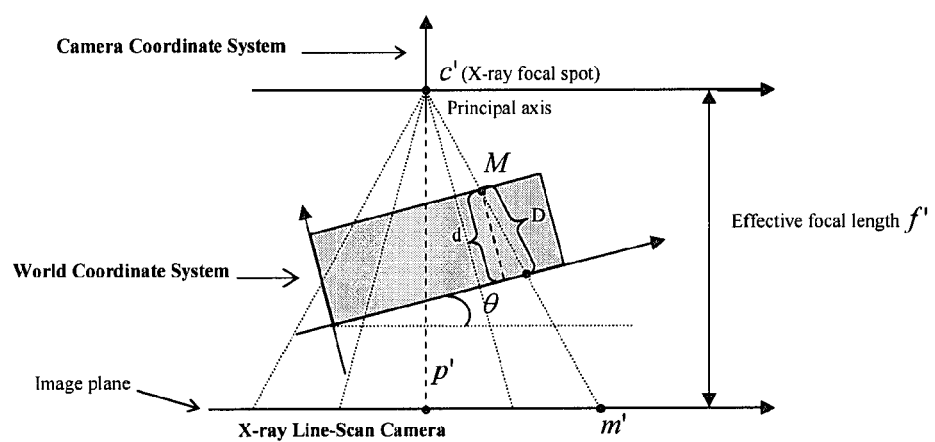
FIG. 7 is a schematic plot depicting pinhole camera geometry for an X-ray camera and the X-ray fan beam effect.

FIG. 7 is a diagram showing a pin-hole model of the x-ray camera and the x-ray fan beam effect. After CCD camera calibration, the laser subsystem can capture the 3D profile of the scanned objects. As shown in FIG. 7, c' depicts the x-ray focal spot which also is the camera center and the origin of camera coordinate system, p' depicts the principle point and f' depicts the effective focal length. M is a point on the object surface and m' is its image in the image plane (detector). $\theta$ is the angle between the conveyor belt and detector image plane. D is the length of one X-ray passed through the object.

In practice, the 3D thickness image is mapped to a pseudo x-ray image which will further be subtracted from the real grabbed x-ray image to remove the thickness influence in the x-ray image, thus highlighting the suspicious areas. For each point at the object surface, the x-ray attenuation is not determined by its distance from the conveyer belt surface (d in FIG. 7); instead the X-ray attenuation is determined by the length of the X-ray pathway through the object (D in FIG. 7). After the X-ray line-scan camera calibration, all the parameters of the X-ray camera are known, (e.g., focal spot location and effective focal length), so the X-ray pathway can be calculated. Thus the X-ray fan beam effect can be compensated.

Figure 8:
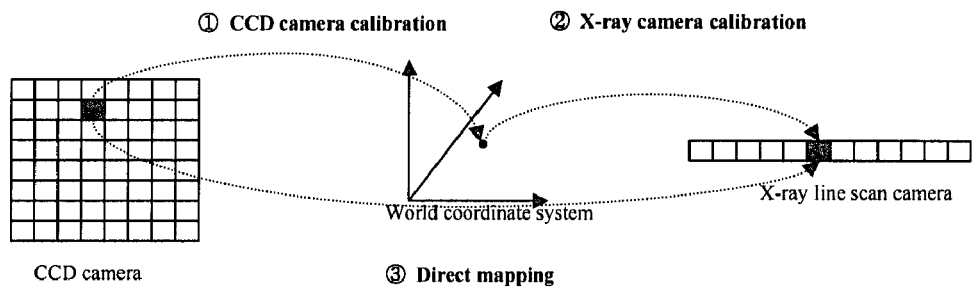
FIG. 8 illustrates direct pixel mapping from the CCD camera to the X-ray line-scan camera.

FIG. 8 illustrates a direct pixel mapping from the CCD camera 6 to the X-ray line-scan camera 4. After CCD camera calibration, every intrinsic and extrinsic parameter of the CCD camera (6, 6', 7, 7') is known. So for each pixel in the image frame of the CCD camera, it is easy to get the corresponding coordinates in the world coordinate system. Furthermore, after X-ray line-scan camera 4 calibration, the image coordinate (in X-ray line-scan camera 4) for each point in world coordinate system is calculated. In addition, by combining two calibration results together, for each pixel in CCD camera, its image coordinate in the X-ray line-scan camera 4 can be directly calculated. By directly mapping pixels in the CCD camera 6 to pixels in the X-ray line-scan camera 4, a lot of computations are saved since there is no need to calculate the translation from CCD image plane to the world coordinate system and from world coordinate system to the X-ray image plane. In other words, the mapping from CCD camera 6 to world coordinate can be realized after CCD camera 6 calibration. The mapping from world coordinate to X-ray line-scan camera 4 can be realized after X-ray camera 4 calibration. The direct mapping from CCD camera 6 to X-ray line-scan camera 4 can be achieved by combining both calibration results.

Figure 9:
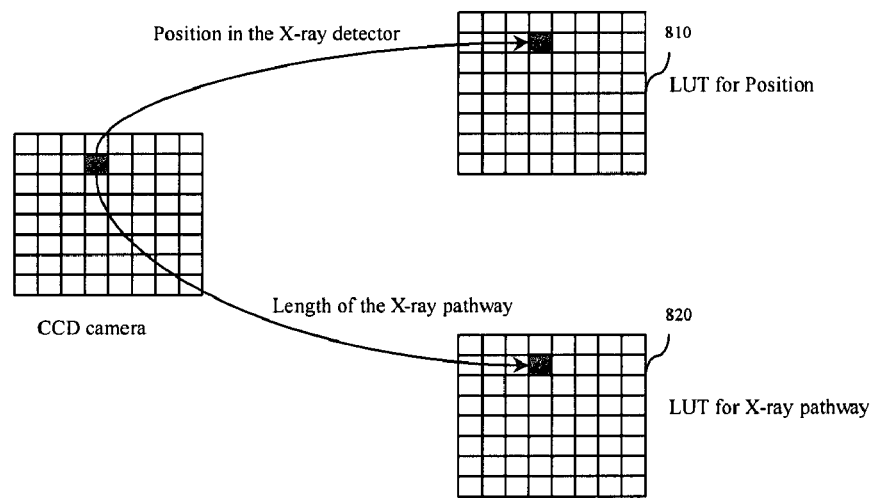
FIG. 9 illustrates lookup tables generated after the CCD and X-ray line-scan camera calibration.

To further save real-time computation, the direct mapping from pixels in the CCD camera 6 to pixels in the X-ray line-scan camera 4 can be implemented by using look up tables (LUT). FIG. 9 illustrates lookup tables generated after CCD and X-ray line-scan camera calibration. LUT 810 contains image position information for each CCD pixel in the detector plane while LUT 820 saves pathway information corresponding to each CCD pixel. By using these two LUTs, for any pixel in CCD camera, its image position in the X-ray detector plane and its corresponding X-ray pathway is known. Thus, direct mapping an image in CCD image plane to the X-ray detector image plane is possible. There are two key benefits realized from using these two LUTs. One is that the expensive runtime computation can be replaced with a simpler lookup operation. The speed gain is significant since retrieving a value from memory is much faster than undergoing an extensive computation. The other is that there is no need to do image registration for images from the CCD cameras 6 and those from the X-ray line-scan camera 4.

Figure 10:
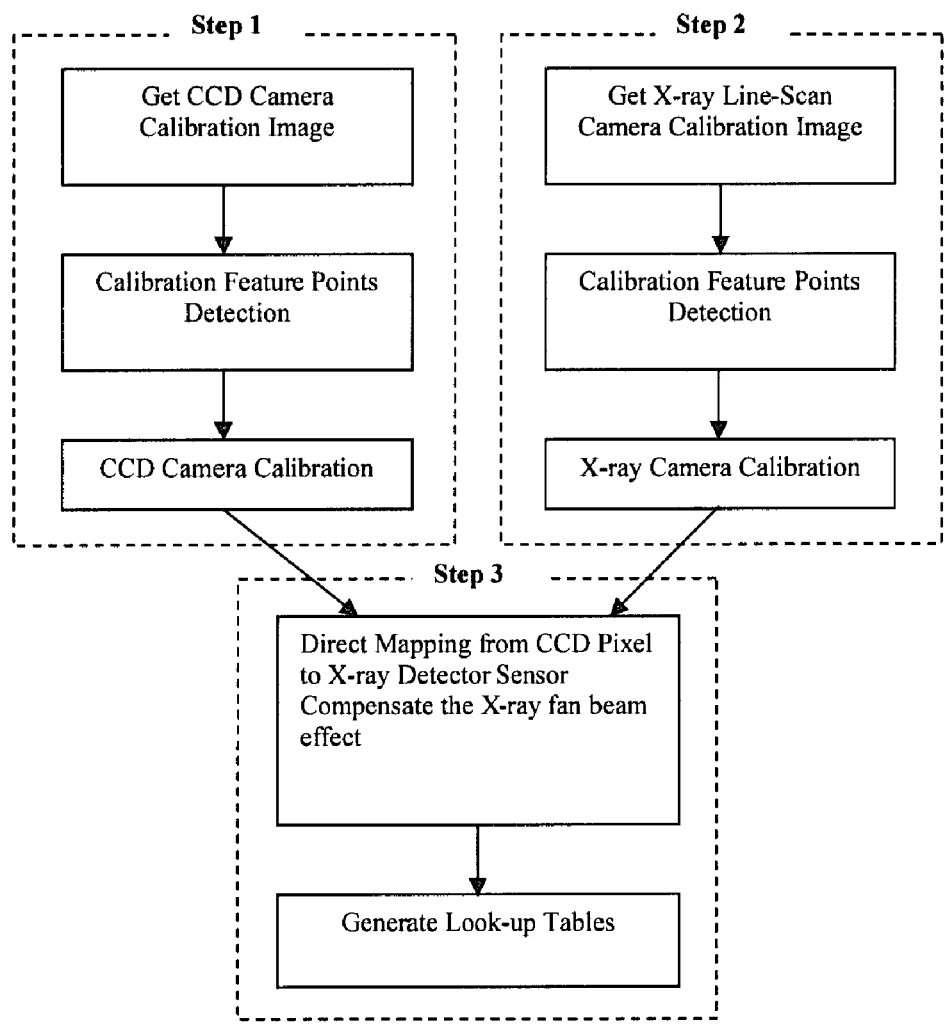
FIG. 10 is a flowchart illustrating the entire calibration procedure.

FIG. 10 is a flowchart illustrating the entire calibration procedure. Step 1 outlines CCD cameras 6 calibration, step 2 shows X-ray line-scan camera 4 calibration and step 3 summarizes direct mapping from CCD pixel to X-ray detector sensor. More specifically, in step 1, the CCD camera calibration image is captured when the plane of the calibration model plate 110 or 120 is coplanar with the laser beam 14. Calibration feature points are then detected and used to calibrate the CCD cameras 6. In step 2, the X-ray line-scan camera calibration image is grabbed when the X-ray beam 15 intersects the steel pins 130 which are inserted at known positions. Their image positions in the X-ray image 340 are then detected which along with their coordinates in the world coordinate system, are used to calibrate the X-ray line-scan camera 4. The X-ray fan beam effect is then compensated. Following the whole calibration procedure, the two lookup tables are generated which will be used in laser range imaging to speed up the performance of the whole system.

How to use the two calibration lookup tables in real-time? One example to use the calibration lookup tables in real-time is shown below (However, this specific procedure does not limit the methodology in general): (1) Grab laser image with CCD camera when object passes through the laser beam. (2) Detect laser stripe in the image from (1). (3) For each pixel on the laser line from (2), use the two lookup tables to get its corresponding position on the X-ray detector plane, and its associated X-ray pathway; and (4) A laser line on the CCD image plane will be mapped to a line on the detector plane. So, several lines from (3) are collected sequentially to generate a laser 3D image with the X-ray fan beam effect compensated.

Figure 11:
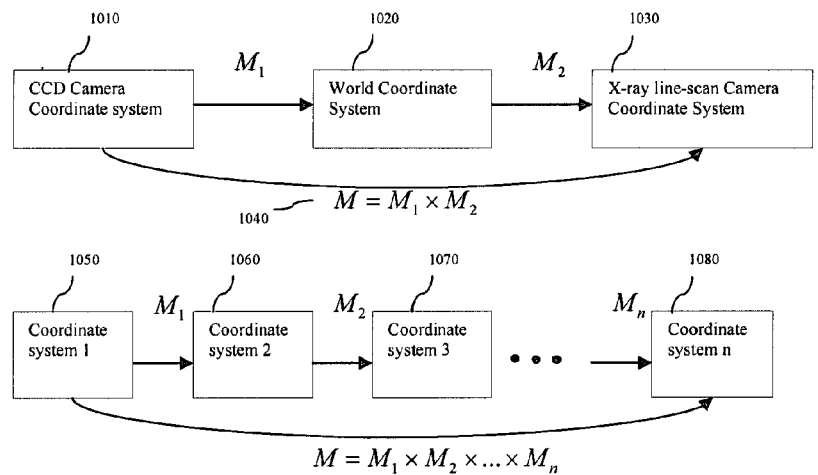
FIG. 11 illustrates a block diagram depicting a pixel mapping method used in the system calibration.

FIG. 11 illustrates a block diagram depicting a pixel mapping method used in the system calibration. Machine vision system usually combines different imaging modality to achieve better performance. Images from different image sensors can not be used directly since they are usually in different scale and in different coordinate system. If sensor mapping can be achieved during system calibration, a lot of computation can be saved. This is critical for most real-time systems. FIG. 10 is the diagram showing the sensor mapping procedure. In the second preferred embodiment, the CCD camera coordinate system 1010 is related with world coordinate system 1020 by matrix $M_1$ during the CCD camera calibration. The world coordinate system 1020 is related with the X-ray line-scan camera system 1030 by matrix $M_2$ during X-ray camera calibration. So using a new matrix $M=M_1 \times M_2$ 1040 can achieve direct mapping from CCD camera coordinate 1010 to X-ray line-scan camera coordinate 1030. By doing so, the image registration work becomes trivial for images from different sub-systems. This method can be easily extern to some application where more than 3 coordinate systems are involved as long as each coordinate pair is related by some matrix $M_i$ (i=1, 2, ... ). The final calibration result can be simplified as the product of all these matrix in sequence $M=M_1 \times M_2 \times \ldots \times M_n$, (n=2, 3, 4, ... ).

Figure 12:
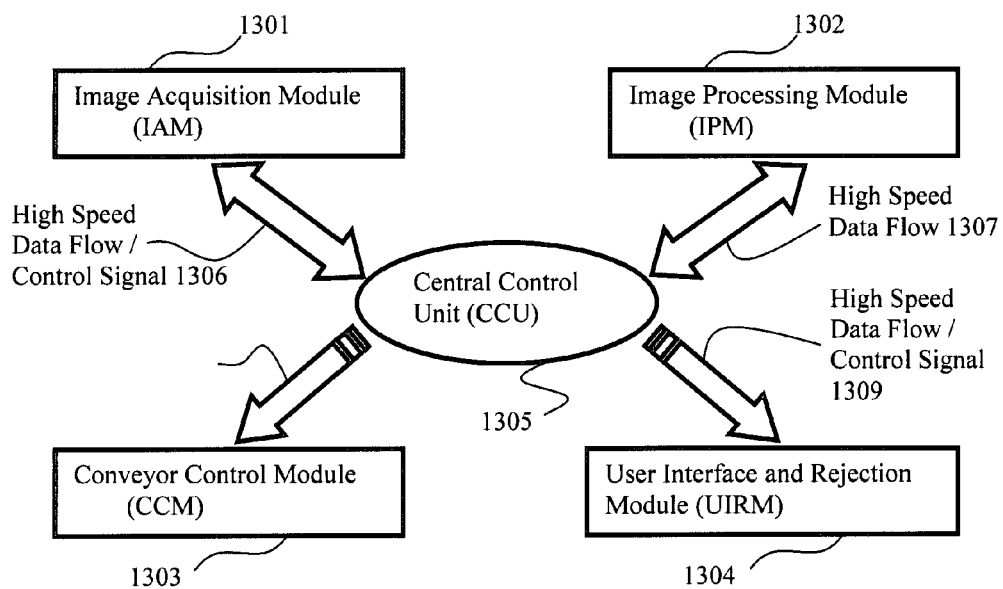
FIG. 12 illustrates a block diagram depicting system data and signal flow according a third preferred embodiment of the present invention, the general procedure includes an Image Acquisition Module (IAM), a Conveyor Control Module (CCM), an Image Processing Module (IPM), a User Interface and Rejection Module (UIRM), and a Central Control Unit (CCU).

FIG. 12 illustrates a block diagram depicting the general procedure of the system employing multiple cameras according to a third preferred embodiment of the present invention. In this embodiment, the general procedure includes an Image Acquisition Module (IAM) 1301, a Conveyer Control Module (CCM) 1303, an Image Processing Module (IPM) 1302, a User Interface and Rejection Module (UIRM) 304, and a Central Control Unit (CCU) 1305. The role of the Central Control Unit (CCU) 1305 is to control and organize the overall data flow as well as the control signals among all the modules within the whole imaging system. In the Image Acquisition Module (IAM) 1301, both X-ray and Laser images are acquired through a high-speed imaging processor once IAM 1301 receives the control signal 1306 from the CCU 1305. The acquired image data is then sent to the CCU 1305 through high-speed data flow 1306 for the further processing. The Image Processing Module (IPM) 1302 processes the image data sent by CCU 1305 through the high-speed data flow 1307. Once the image processing work is done, the results will be sent back to the CCU 1305 through 1307. The CCU 1305 then sends the results and the control signal 1309 to the User Interface and Rejection Module (UIRM) 1304. The role of UIRM 1304 is to display the results and related statistics on the computer monitor as well as dispatch the control signal 1309 to the rejection mechanism to reject the defected samples. The role of Conveyor Control Module (CCM) 1303 is to control moving direction, running speed of the conveyor according to the control signal 1308 sent by CCU 1305. The IAM 1301 and CCM 1303 are perfectly controlled and synchronized by the CCU 1305 such that high resolution images can be acquired without sacrificing the throughput (running speed) of the imaging system.

Figure 13:
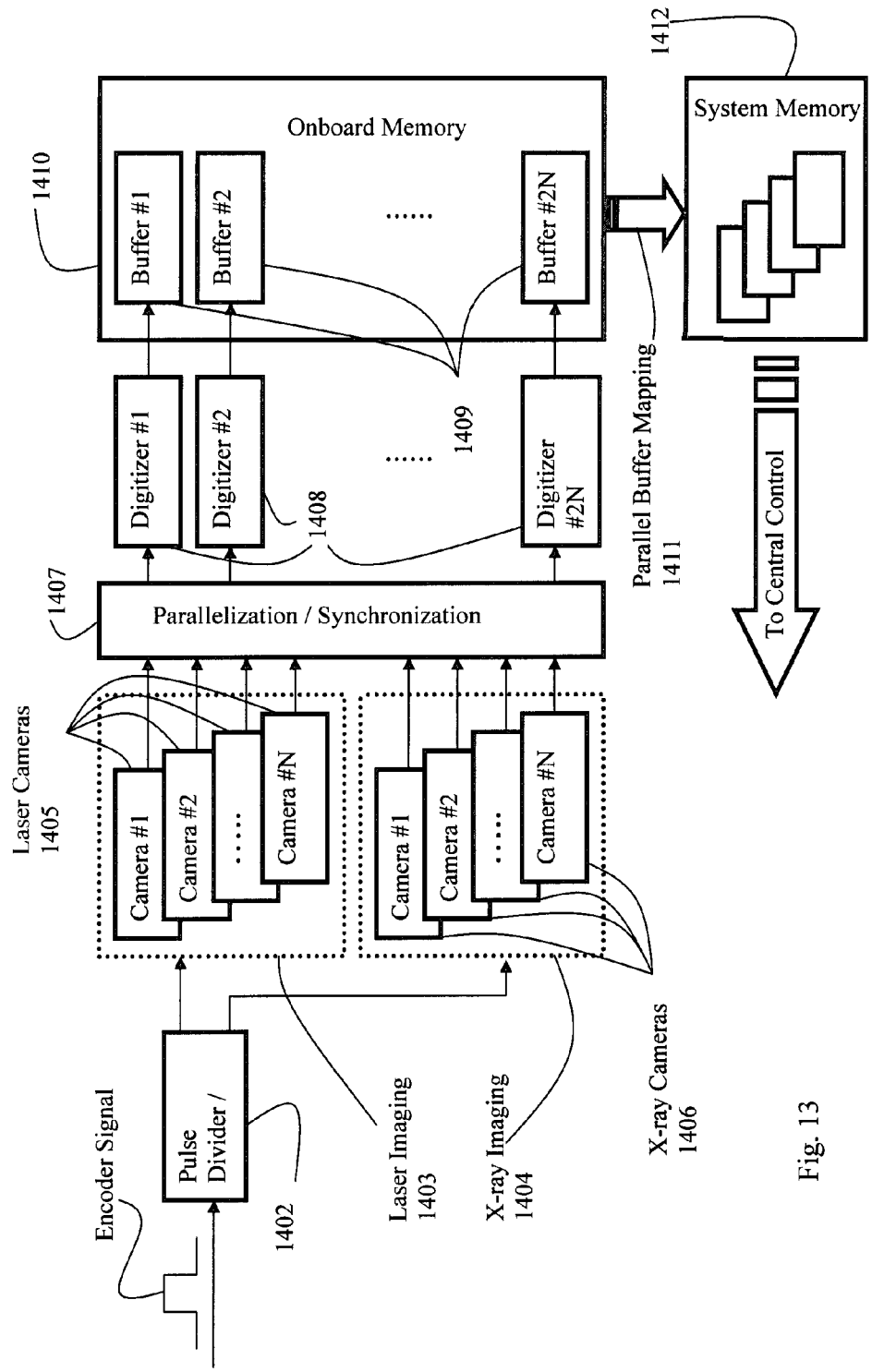
FIG. 13 illustrates a more detailed schematic representation of the Image Acquisition Module, which receives a trigger signal and provides acquired image data to the Central Control Unit.

A more detailed schematic description of Image Acquisition Module (IAM) 1301 is shown in FIG. 13. The IAM 1301 is driven by the encoder signal 1401 from the running conveyor 3. A Pulse Divider/Synchronizer then distributes the encoder signal 1401 to the both Laser imaging module 1403 and X-ray imaging module 1404 such that these two modules are perfectly synchronized. Each imaging module includes multiple cameras 1405, 1406, which capture corresponding images not only at a very high speed rate, but also at the same time. All the captured images are then sent to the corresponding digitizers 1408 in a parallel and synchronized way by parallelization/synchronization 1407. The role of digitizers is to digitize all the incoming analogue image signals to the binary data and put them into the consequent buffers 1409 on the onboard memory 1410. The onboard memory 1410 is then mapped to its corresponding system memory 1412 through parallel buffer mapping 1411 such that the acquired image data can finally be accessed and processed by CCU 1305.

Figure 14:
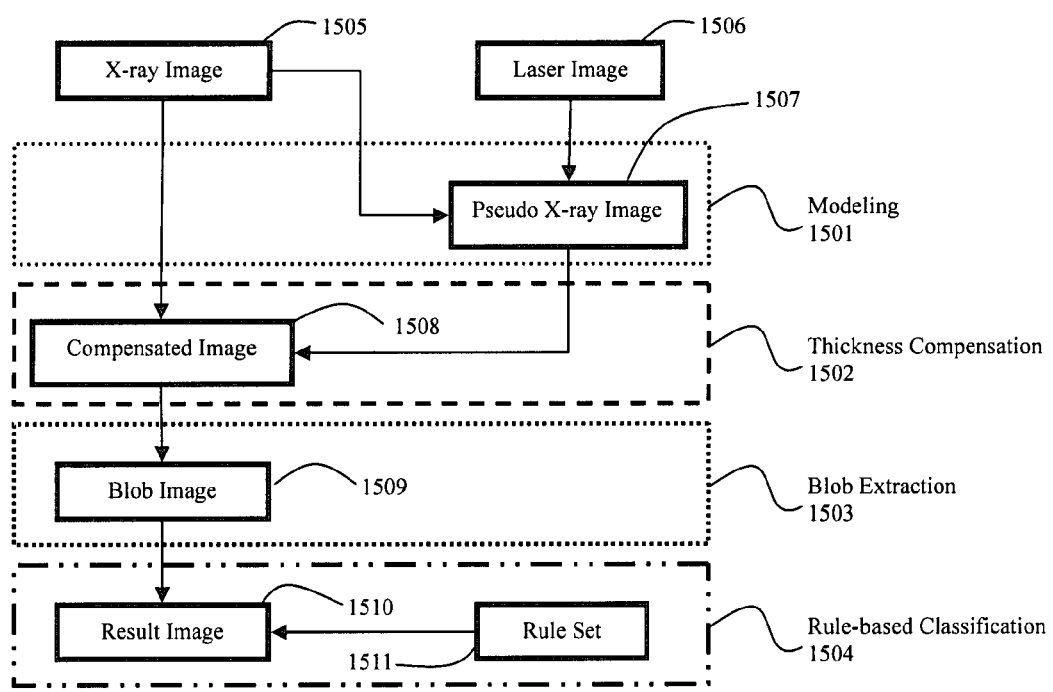
FIG. 14 is a flowchart illustrating a processing carried out by the Image Processing Module, which receives both laser and x-ray image data from the Image Acquisition Module, combines the information from both images, identifies the defected samples, and sends the result data to the Central Control Unit.

A more detailed procedure of intrusion detection performed by the Image Processing Module (IPM) 1302 in the imaging system is shown in FIG. 14. The overall procedure is composed of four steps. Both X-ray images 1505 and Laser images 1506 are acquired through a high-speed, high-definition imaging processor in the Image Acquisition Module (IAM) 1301. The image data is then transferred to IPM 1302 through CCU 1305. In the modeling step 1501, the acquired Laser image 1506 is converted to a Pseudo X-ray image 1507 based on both x-ray 1505 and laser images 1506 acquired in IAM 1301. In the thickness compensation step 1502, the original x-ray image 1505 acquired in 1301 is compensated by Pseudo X-ray image 1507 formulated in modeling step 1501. The compensated image 1508 is then fed into blob extraction step 1503 to extract the region of interest (blobs) 1509 of the testing sample. Finally, in the Rule-based Classification step 1504, blobs in the compensated image 1508 are analyzed and the features of each blob are fed to the rule-based classifier 1511, where each blob is classified as either normal (sample tissue) or abnormal (intrusion, which can be, but not limited to be bone fragments, metal, glass, etc.) based on a set of predefined rules 1511. Once intrusions are found and recorded in the result image 1510, the IPM 1302 will report the locations of those defects to the CCU 1305, which then send the control signal as well as the result data 1510 to the User Interface and Rejection Module (UIRM) for the defected sample display and rejection purposes.

Figure 15:
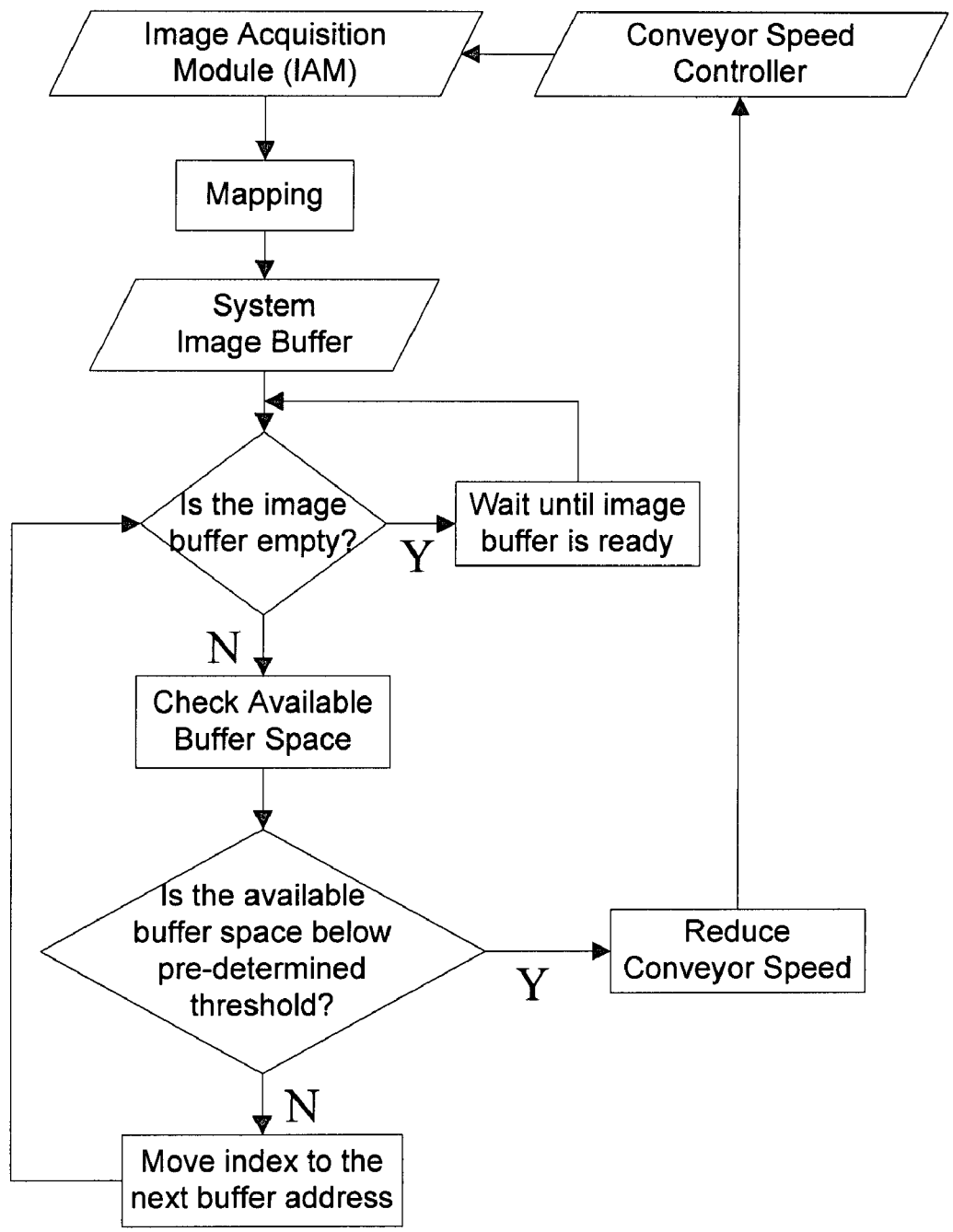
FIG. 15 is a flowchart illustrating the process of the Interface and Rejection Module controlling the speed of the conveyor based on the free buffer memory space available in the Image Acquisition Module.

Sometimes when the system is running, it is possible that delays occur in the system due to overloaded data. Aforementioned delays may have negative effects on the system performance, such as reduced throughput, decreased processing accuracy, missing data, etc. To prevent such negative effects from happening, FIG. 15 shows the general flowchart of the data overflow protection mechanism for the system. The onboard to system buffer mapping and data processing are two parallel procedures. They work independently and simultaneously. If the speed of data processing is slower than that of data mapping, the mapped data on the system memory will eventually overflow. The data overflow protection mechanism resolve this problem by periodically checking the available buffer space on the system memory to see whether the size of free buffer space is below some predetermined threshold. If it is the case, a control signal will be sent to the conveyor belt controller to temporary reduce the running speed of the conveyor. By doing this the speed of imaging acquisition will be reduced, and as the result, the onboard to system buffer mapping speed will be reduced correspondingly.

Figure 16:
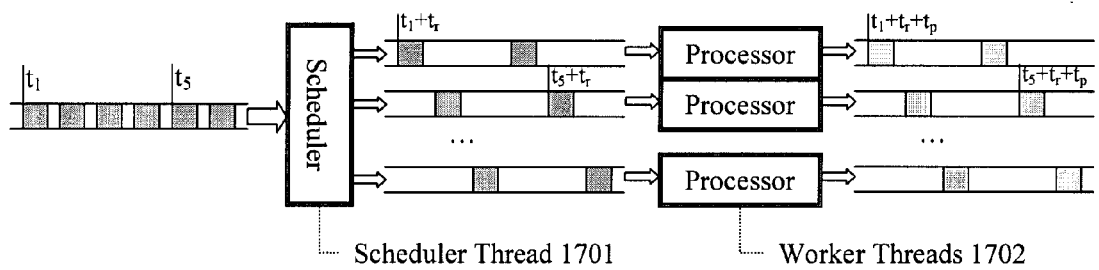
FIG. 16 illustrates a configuration of a multi-thread parallel-processing model used in the third preferred embodiment of the present invention.

In the system, because the workload is heavy due to the combined X-ray and laser imaging algorithms, and the high input data rate, a multithread model is used, as seen in FIG. 16, in order to ensure timely response. In this multithread model, the tasks are shared by different threads, i.e., a scheduler thread 1701 and a set of worker threads 1702. When a new image data arrives, the scheduler 1701 will respond first if it is ready, pass the job to a free worker thread 1702, and then get ready for the next frame. When a worker thread 1702 is called by the scheduler thread 1701, it will enter the busy state and process the assigned image data. After the processing is finished, the worker will feed the processed result back to the scheduler and return to the free state. The time constraint for the proper processing is $t_f > t_r$, where $t_f$ is the time interval between the start of the image being processed and the start of its successor, and $t_r$ is the scheduler response time for the current image, which is far less then the processing time $t_p$ for the image. The advantage of this multithread model is that the scheduler thread 1701 can always respond in time to the incoming image frames as long as there are sufficient free worker threads 1702. Comparing this approach with the single thread approach, this space-for-time multithread approach significantly promotes real-time capability and system resource utilization.

Figure 17:
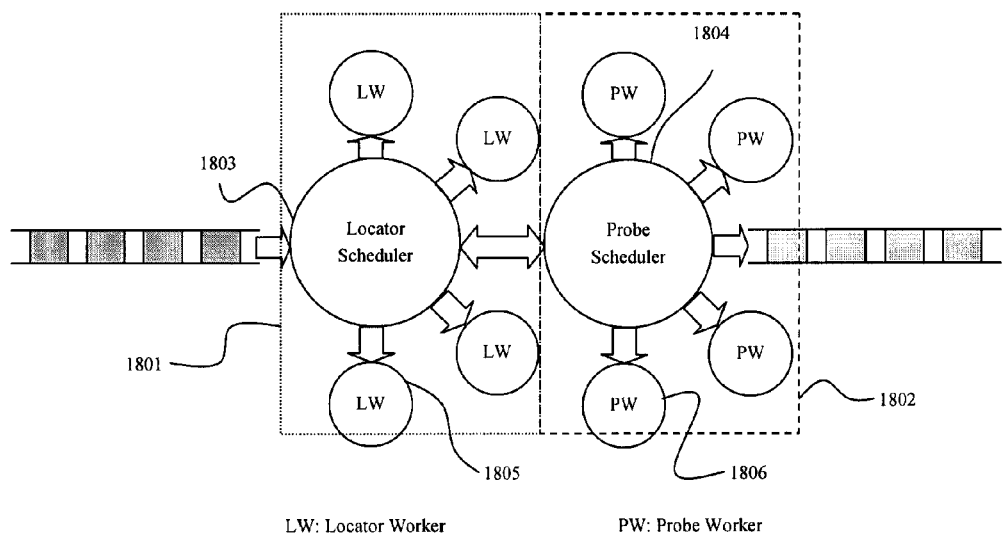
FIG. 17 illustrates a more a detailed configuration the multi-thread parallel-processing model, which consists of two nested structure to realize efficient parallel processing.

In the multithread scheme, the threads are organized in a nested manner. As shown in FIG. 17, the threads are grouped into two sets, namely a locator group 1801 and a probe group 1802. The locator group 1801 consists of one Locator Scheduler 1803 and multiple Locator Workers 1805, similarly the probe group consists of one Probe Scheduler 1804 and multiple Probe Works 1806. For the worker threads in both groups, the scheduler thread serves as an interface passing the input and output data, and as a coordinator managing workloads. The function of the locator group 1801 is to determine the location of each sample, in terms of the X-Y coordinates and dimensions. The probe group 1802 is set to search for physical hazards or bone fragments in each sample passed by locators, based on the information embedded in the X-ray and laser range images.

The control mechanism of the multithread system can be described as three phases, as shown in FIG. 18(a)-18(c). For convenience, Scheduler L stands for the scheduler in the locator group, and Scheduler P means the scheduler in the probe group.

Initialization phase, as shown in FIG. 18(a):
1. Each worker thread finishes its own initialization and sends a READY message to its scheduler.
2. Scheduler thread signals READY to controller when all worker threads are ready. Processing phase, as shown in FIG. 18(b):
For Locator Group
1. When a new image frame comes, scheduler L immediately selects a free locator worker, prepares the private working buffer for the worker and sends a START message to it. Then the selected locator worker starts working on the image frame, and scheduler L becomes ready for the next incoming frame once it is confirmed that the locator worker has started working.
2, Once a locator finishes working on an image frame, it will register the result information, send a READY message to scheduler L, and start waiting for the next job. If a new object is found, the locator thread will send a FOUND message to the scheduler in the probe group (scheduler P) before taking a break.
For Probe Group
1. When a FOUND message is received by Scheduler P, it immediately selects a free probe worker and prepares the private working buffer for the worker and sends a START message to it. The selected probe worker will start working on the object, while scheduler P becomes ready for the next object.
2. Similar to the locator case, once a probe worker finishes working on an object, it will register the result information, and send a READY message to Scheduler P. If the probe finds one or more physical hazardous items, such as a bone fragment, or a metal clip, etc., it will report the existence and location of each detected item.

Termination phase, as shown in FIG. 18(c):
1. User sends STOP message to the scheduler of the locator group (i.e., scheduler L).
2. Scheduler L sends STOP message to each of the locator workers if the worker is ready (i.e., has not job in hand).
3. Scheduler L sends STOP message to scheduler P after all the locator workers are stopped.
4. Scheduler P sends STOP message to each of the probe workers if the worker is ready.
5. Scheduler P sends FINISH message to scheduler L after all the probe workers are stopped, and scheduler L will then send FINISH message to controller.
6. send FINISH message to controller.

What is claimed is:
1. An inspection apparatus, comprising;
a housing including:
an x-ray source for generating an x-ray beam;
a first laser for generating a first laser beam;
a second laser for generating a second laser beam,
wherein the first and second lasers are placed on each side of said x-ray source,
wherein said x-ray beam and said first and second laser beams are substantially coplanar,
wherein the first and second laser beams overlap each other, and
wherein said housing further includes:
a first window;
a pair of cameras;
a second window; and
a third window,
wherein said x-ray beam and said first and second laser beams pass through said first window,
wherein each camera of said pair of cameras is located on one side of said x-ray source, respectively, and
wherein one camera of said pair of cameras is oriented towards said second window and the other camera of said pair of cameras is oriented towards said third window,
said inspection apparatus further comprising:
a conveyor for carrying object(s) for inspection;
an x-ray line scan camera that is placed under the conveyor and is aligned with the x-ray beam for capturing an x-ray image of said object(s) radiated by the x-ray beam,
an encoder that is attached to said conveyer and sends conveyor movement signals to a computer; and
a rejection device for removing object(s) off said conveyor;
wherein said pair of cameras capture image data of said object(s) when irradiated by said first and second laser beams,
said computer including;
means for receiving said signals from said encoder;
means for synchronizing said pair of cameras and said x-ray line scan camera based on said received encoder signals;
means for receiving image data of said object(s) from said pair of cameras and an x-ray image from said x-ray line scan camera;
means for generating an x-ray image of said object(s);
means for calculating intensity, inverse intensity, and x-ray absorption coefficient of said x-ray image;
means for generating a depth image of said object(s), said depth image having a thickness intensity;
means for calculating a virtual x-ray intensity image of said object(s), wherein said virtual x-ray image is obtained through a regression analysis based on said x-ray absorption coefficient and said thickness intensity;
means for subtracting said inverse intensity of said x-ray image from said virtual x-ray image to detect bone, bone fragments or foreign materials in the object(s); and
means for generating a rejection signal when it is detected that said object(s) include bones, bone fragments or foreign materials;
wherein the rejection signal is sent by said computer to said rejection device to remove said object(s) detected with bone, bone fragments or foreign materials from said conveyor.

2. A calibration model for calibrating said pair of cameras and said x-ray line scan camera of claim 1, said calibration model comprising:
two plates each with calibration holes,
wherein pins are inserted in the calibration holes of the two plates, and wherein the two plates are used to calibrate said pair of cameras and the pins are used to calibrate the x-ray line scan camera.

3. A method of using the calibration model of claim 2 to calibrate said pair of cameras and the x-ray line scan camera, comprising the steps of:
aligning the calibration model with the first and second laser beams and the x-ray fan beam;
using said encoder to synchronize said pair of cameras and the x-ray scan camera to capture images by said pair of cameras and said x-ray line scan camera of said calibration model when it is moving on said conveyor; and
using said captured images of said calibrating model to calibrate said pair of cameras and said x-ray line scan camera.

4. An imaging system, comprising:
an image acquisition module which acquires x-ray and laser images of object(s), said image acquisition module including a laser imaging module and an x-ray imaging module, said laser imaging module and said x-ray imaging module including a plurality of cameras for capturing respective laser and x-ray images of said object(s) at the same time,
a conveyor control module which controls the speed of a conveyor on which said object(s) are placed;
an image processing module which processes the laser and x-ray image data captured by the image acquisition module to determine if said object(s) are defective;
a rejection module which dispatches a control signal to a rejection mechanism to reject the defective object(s) from said conveyor; and
a control module which controls the interaction between said image acquisition module, said conveyor control module, said image processing module and said rejection module,
wherein said image processing module further converts said laser image into a pseudo x-ray image based on both the acquired laser and x-ray images, compensates for the thickness of said pseudo x-ray image, extracts a region of interest(s) from said compensated pseudo x-ray image to create a blob image(s), and classifies said blob image(s) as normal or abnormal.

5. The imaging system according to claim 4, wherein said image acquisition module further includes a buffer memory for storing said capturing laser and x-ray images.

6. The imaging system according to claim 5, wherein said control module compares free buffer space of said buffer memory to a predetermined threshold and a sends a control signal to said conveyor control module to decrease the speed of said conveyor when said free buffer space of said buffer memory is below said predetermined threshold.

7. The imaging system according to claim 6, wherein at least one of said image acquisition module, said conveyor control module, said image processing module, said rejection module, and said control module implements a multithread model, which includes a scheduler thread and a worker thread.

8. The imaging system according to claim 7, wherein said scheduler thread passes newly arrived image data to a worker thread, and said worker thread enters a busy state to process the passed image data, wherein the response time of the scheduler thread is less than the processing time of the worker thread.

9. The imaging system according to claim 8, wherein said threads of said multithread model are organized in a nested manner.

10. The imaging system according to claim 8, wherein said thread are grouped into a locator group, which is to used determine the location of each sample and a probe group, which is set to search for physical hazards or bone fragments in each sample based on the information embedded in the x-ray and laser range images.

11. A calibration model for calibrating said imaging system of claim 4, said calibration model comprising:
two plates each with calibration holes,
wherein pins are inserted in the calibration holes of the two plates, and wherein the two plates and the pins are used to calibrate the plurality of cameras.

12. The calibration model according to claim 11, wherein said laser imaging module includes a first laser for generating a first laser beam, a second laser for generating a second laser beam and an x-ray source for generating an x-ray beam,
wherein said plurality of cameras includes a pair of camera and an x-ray line scan camera.

13. A method of using the calibration model of claim 12 to calibrate the pair of cameras and the x-ray line scan camera, comprising the steps of:
aligning the calibration model with the first and second laser beams and the x-ray fan beam;
using an encoder to synchronize the pair of cameras and the x-ray scan camera to capture images by the pair of cameras and the x-ray line scan camera of the calibration model when the calibration model is moving on said conveyor; and
using the captured images of the calibrating model to calibrate the pair of cameras and the x-ray line scan camera.

14. The inspection apparatus according to claim 1, wherein said first and second laser sources are each titled at an angle to allow said pair of cameras to capture respective sides of the object(s) illuminated by said first and second laser sources.

15. The imaging system according to claim 4, wherein said rejection module includes a user interface module which displays related statistics regarding defective samples.

16. The imaging system according to claim 4, wherein said conveyor control module and said image acquisition module are synchronized by the control module in order to increase the throughput of the said imaging system.

* * * * *